United States Patent [19]

Giles et al.

[11] Patent Number: 4,545,987

[45] Date of Patent: Oct. 8, 1985

[54] PSORALEN INACTIVATED DOUBLE-STRANDED RNA VIRAL VACCINES

[75] Inventors: Richard E. Giles, Alameda; David R. Stevens, Fremont; Gary P. Wiesehahn, Alameda, all of Calif.

[73] Assignee: Advanced Genetics Research Institute, Oakland, Calif.

[21] Appl. No.: 563,939

[22] Filed: Dec. 20, 1983

[51] Int. Cl.[4] .............................................. A61K 39/12
[52] U.S. Cl. .................................... 424/89; 435/235; 435/238
[58] Field of Search .................. 435/235, 238; 424/89

[56] References Cited

PUBLICATIONS

Theiler, Vet. J., (1980), 64:600–607.
Kemeny and Drehle, Am. J. Vet. Res., (1961), 22:921–925.
Alexander and Haig, Onderstepoort J. Vet. Res., (1951), 25:3–15.
Parker et al., Vet. Rec., (1975), 96:284–287.
Isaacs et al., Biochemistry, (1977), 16:1058–1064.
Hearst and Thiry, Nucleic Acids Res., (1977), 4:1339–1347.
Hanson et al., J. Gen. Virol., (1978), 40:345–358.
Talib and Banerjee, Virology, (1982), 118:430–438.
Hanson, Medical Virology II, Proceedings of the 1982 International Symposium on Medical Virology, de la Maza and Peterson, eds., New York: Elsevier Biomedical, 1983, pp. 45–75.
J. Parker et al., (1975), Vet. Rec. 96:284–287.
J. L. Stott, et al., (1979), Proc. Annu. Meet US Anim Health Assoc., 177:55–62.
B. I. Osburn et al., and J. L. Stott et al., (1979), Fed. Proc. 38 (3 part 1) 1091 Coden: FEPRA.

Primary Examiner—Shep K. Rose
Attorney, Agent, or Firm—Townsend & Townsend

[57] ABSTRACT

Novel vaccines of double-stranded RNA viruses are prepared by psoralen inactivation under mild conditions in an inert atmosphere, optionally in the presence of a mild singlet oxygen scavenger. The resulting inactivated virus can be used as a vaccine for inoculation of hosts to provide for the stimulation of the immune system to the virus.

11 Claims, No Drawings

PSORALEN INACTIVATED DOUBLE-STRANDED RNA VIRAL VACCINES

BACKGROUND OF THE INVENTION

1. Field of the Invention

The disease Bluetongue is a systemic viral infection of ruminants, such as sheep and cattle. The Bluetongue virus (BTV) is transmitted by small biting flies and is known to occur in twenty serotypic variants that do not provide cross-protection immunologically.

The Bluetongue virus is the prototype orbivirus and is composed of ten double-stranded RNA genomic segments. Bluetongue virions have an inner capsid of five polypeptides and a diffuse non-enveloped outer layer containing two polypeptides. It is found that variable amino acid sequences in P2, the major surface polypeptide, are responsible for immunologic serotype specificity. A core protein, P7, is detected by the complement fixation assay and determines cross-reacting group specificity.

In the United States, the primary serotypes observed are 11 and 17, with serotypes 2, 10 and 13 being observed less frequently.

The first vaccine for BTV was an attenuated live virus vaccine, which has been utilized over forty years in South Africa. Other modified live virus Bluetongue vaccines have also been reported. These attenuated live virus vaccines induce teratogenic lesions in fetuses and may also result in the emergence of recombinant virus strains. There is, therefore, need for an effective vaccine against Bluetongue, which provides protection to an inoculated mammalian host, without the hazards observed with attenuated live Bluetongue virus.

2. Description of the Prior Art

Theiler, *Vet. J.* (1908) 64:600–607 describes an attenuated live Bluetongue virus vaccine. Kemeny and Drehle, *Am. J. Vet. Res.* (1961) 22:921–925 describe a tissue culture-propagated BTV for vaccine preparation. Alexander and Haig, *Onderstepoort J. Vet. Res.* (1951) 25:3–15 describe the use of attenuated BTV in the production of a polyvalent vaccine for sheep. Parker *et al.*, *Vet. Rec.* (1975) 96:284–287 describe an inactivated vaccine against Bluetongue.

Isaacs *et al.*, *Biochemistry* (1977) 16:1058–1064, describe the synthesis of several psoralen derivatives and their photoreactivity with double-stranded RNA. Hearst and Thiry, *Nucleic Acids Research* (1977) 4:1339–1347; Hanson *et al.*, *J. Gen. Virol.* (1978) 40:345–358; and Talib and Banerjee, *Virology* (1982) 118:430–438, describe the photoreactivity of various psoralen derivatives with animal viruses. Hanson, in *Medical Virology II, Proceedings of the 1982 International Symposium on Medical Virology*, de la Maza and Peterson, eds., New York: Elsevier Biomedical, 1983, pp. 45–75, has cited unpublished data on the inactivation of Bluetongue virus utilizing psoralen photochemistry.

SUMMARY OF THE INVENTION

Vaccines are provided for inoculation against Bluetongue virus, which inactivated vaccines are prepared by irradiating the virus suspension with light in the presence of psoralen in an inert atmosphere for a time sufficient to completely inactivate the virus. The resulting inactivated virus suspension may then be stored for subsequent use.

DESCRIPTION OF THE SPECIFIC EMBODIMENTS

Vaccines are provided for inoculation of ruminants against Bluetongue. The vaccines are prepared by inactivation of one or more serotypes of Bluetongue virus (BTV), a multisegmented double-stranded RNA orbivirus. The BTV is inactivated by combining a suspension of the BTV in an appropriate medium with a sufficient amount of a psoralen to provide for complete inactivation of BTV upon irradiation with long wavelength ultraviolet light (UVA), while maintaining an inert atmosphere. The resulting inactivated virus preparation may be stored until used for inoculation. Inoculated ruminants react to vaccination with the subject vaccine by producing neutralizing antibodies.

Any of the serotypes of BTV may be inactivated by the subject method. Serotypes of particular interest include 2, 10, 11, 13 and 17, which are the serotypes observed most frequently in the United States, but the other serotypes prevalent in other geographic areas can also be employed.

In preparing the vaccine, the BTV is grown in cultured mammalian cells. Illustrative cells include Vero cells, monkey kidney cells, CCL 10 hamster cells, LMTK⁻cells, or other cells permissive for BTV which can be grown in vitro as monolayer cultures or in suspension culture. The host cells are grown to nominally 80% saturation density, and infected with BTV at a lower muliplicity of infection (MOI) generally less than about 0.05, and more than about 0.005, preferably about 0.01. After adsorbing the viral inoculum to the cells by incubation for a limited period of time at a temperature in the range of about 35° to 40° C., an appropriate mammalian cell growth or maintenance medium is added and the cells incubated at a temperature in the range of about 35° to 40° C., in the presence of about 5% carbon dioxide in air for sufficient time to observe that at least 50% of the cell culture exhibits cytopathic effect (CPE). The CPE is characterized by cell rounding (in monolayers), cell detachment (from monolayers) and cell degeneration.

The crude cell lysate is allowed to incubate overnight at a temperature in the range from about 0° to 5° C. The material is harvested and collected by low speed centrifugation. The resulting pellet is extracted several times in an appropriate buffer, at a pH in the range from about 8 to 9.5, preferably about 8.5 to 9. The extracted pellet suspension is centrifuged at low speed and the supernatant containing the virus is collected. The pellet may be extracted repeatedly with buffer to enhance the total yield of virus. The virus-containing liquid is then clarified by low speed centrifugation, retaining the virus suspended in the liquid, which may then be stored at 4° C.

Tris buffer (2 mM pH 8.8) may be used as the extraction and storage buffer, although other appropriate buffers which will not interfere with the subsequent processing may be used.

The particular medium which is used for the growth of the cells will be a conventional mammalian cell culture medium, such as Eagle's Minimum Essential Medium or Medium 199, usually supplemented with additives such as broth prepared from dehydrated standard microbial culture media, fetal bovine serum, calf serum, or the like.

The compounds which are used for viral inactivation are furocoumarins. These compounds are primarily illustrated by the class of compounds referred to as psoralens, which includes psoralen and derivatives thereof, where the substituents will be: alkyl, particularly of from 1 to 3 carbon atoms, e.g., methyl; alkoxy, particularly of from 1 to 3 carbon atoms, e.g., methoxy; and substituted alkyl, of 1 to 6, more usually 1 to 3 carbon atoms having from 1 to 2 heteroatoms, which will be oxy, particularly hydroxy or alkoxy of from 1 to 3 carbon atoms, e.g., hydroxymethyl and methoxymethyl; or amino, including mono- and dialkyl amino or aminoalkyl, having a total of from 0 to 6 carbon atoms, e.g., aminomethyl. There will be from 1 to 5, usually 2 to 4 substituents, which will normally be at the 4, 5, 8, 4' and 5' positions, particularly at the 4'-position. Illustrative compounds include 5-methoxypsoralen; 8-methoxypsoralen (8-MOP); 4, 5', 8-trimethylpsoralen (TMP); 4'-hydroxymethyl-4,5',8-trimethylpsoralen (HMT); 4'-aminomethyl-4,5',8-trimethylpsoralen (AMT); 4-methylpsoralen; 4,4'-dimethylpsoralen; 4,5'-dimethylpsoralen; 4',8-dimethylpsoralen; and 4'-methoxymethyl-4,5',8-trimethylpsoralen. Of particular interest is AMT.

The furocoumarins may be used individually or in combination. Each of the furocoumarins may be present in amounts ranging from about 0.01 μg/ml to 1 mg/ml, preferably from about 0.5 μg/ml to 100 μg/ml, there not being less than about 1 μg/ml nor more than about 1 μmg/ml of furocoumarins.

In carrying out the invention the furocoumarin(s), in an appropriate solvent which is substantially inert and sufficiently polar to allow for dissolution of the furocoumarin(s), is (are) combined with the viral suspension, conveniently a viral suspension in an aqueous buffered medium, such as used for storage. The amount of virus will generally be about $1 \times 10^6$ to $10^{10}$, more usually about $1 \times 10^7$ to $10^9$ and preferably about $1 \times 10^8$ to $5 \times 10^8$ pfu/ml. The furocoumarin will be at a concentration of about 0.001 mg/ml to 0.5 mg/ml, more usually about 0.05 mg/ml to 0.2 mg/ml. The amount of solvent which is used to dissolve the furocoumarin will be sufficiently small so as to readily dissolve in the aqueous viral suspension and have little, if any, effect on the results.

The psoralen may be added to the viral suspension in a signal addition or in multiple additions, where the virus is irradiated between additions. Usually, the number of additions will be from about 1 to 5, more usually from about 1 to 4, and preferably from about 2 to 4. The total amount of psoralen which will be added will be sufficient to provide a concentration of at least about 0.01 mg/ml to about 1 mg/ml, usually not more than about 0.75 mg/ml and preferably not more than about 0.5 mg/ml. Since a substantial proportion of the psoralen will have reacted with the RNA between additions, the total concentration of psoralen in solution will generally not exceed about 0.1 mg/ml.

The total time for the irradiation will vary depending upon the light intensity, the concentration of the psoralen, the concentration of the virus, and the manner of irradiation of the virus, where the intensity of the irradation may vary in the medium. The total time will usually be at least about 2 hrs. and not more than about 60 hrs., generally ranging from about 10 hrs. to 50 hrs. The times between additions of psoralen, where the psoralen is added incrementally, will generally vary from about 1 hr. to 24 hrs., more usually from about 2 hrs. to 20 hrs.

The temperature for the irradiation is preferably under 25° C., more preferably under 20° C. and will generally range from about −10° to 15° C., more usually from about 0° to 10° C.

The irradiation is normally carried out in an inert atomsphere, where all or substantially all of the air has been removed. Inert atmospheres include nitrogen, helium, argon, etc.

The light which is employed will generally have a wavelength in the range from about 300 nm to 400 nm. The intensity will generally range from about 0.1 mW/cm$^2$ to about 5 W/cm$^2$.

Optionally, a small amount of a singlet oxygen scavenger may be included during the virus inactivation. Singlet oxygen scavengers include ascorbic acid, dithioerythritol, sodium thionite, glutathione, etc. The amount of scavenger will generally be at a concentration of about 0.001 M to 0.5 M, more usually at about 0.05 M to 0.2 M, where the addition may be made in a single or multiple additions.

During irradiation, the medium may be maintained still, stirred or circulated and may be either continuously irradiated or be subject to alternating periods of irradiation and non-irradiation. The circulation may be in a closed loop system or in a single pass system ensuring that all of the sample has been exposed to irradiation.

It may be desirable to remove the unexpened furocoumarin and/or its photobreakdown products from the irradiation mixture. This can be readily accomplished by one of several standard laboratory procedures such as dialysis across an appropriately sized membrane or through an appropriately sized hollow fiber system after completion of the irradiation. Alternatively, one could use affinity columns for one or more of the low molecular weight materials to be removed.

The inactivated vaccine may then be formulated in a variety of ways for use for inoculation. The concentration of the virus will generally be from about $10^6$ to $10^9$ pfu/ml, as determined prior to inactivation. The vaccine may include cells or may be cell-free. It may be in an inert physiologically acceptable medium, such as ionized water, phosphate-buffered saline, saline, or the like, or may be administered in combination with a physiologically acceptable immunologic adjuvant, including but not limited to mineral oils, vegetable oils, mineral salts and immunopotentiators, such as muramyl dipeptide. The vaccine may be administered subcutaneously, intramuscularly, or intraperitoneally. Usually, a specific dosage at a specific site will range from about 0.1 ml to 4 ml, where the total dosage will range from about 0.5 ml to 8 ml. The number of injections and their temporal spacing may be highly variable, but usually 1 to 3 injections at 1, 2 or 3 week intervals are effective.

The following examples are offered by way of illustration and not by way of limitation.

EXPERIMENTAL

Virus Growth and Tissue Culture

Hamster cells [BHK-21 (C-13), American Type Culture Collection, (CCL 10)] are grown as monolayers in plastic cell culture vessels in Eagle's Minimum Essential Medium with Earle's Salts (MEM) and non-essential amino acids (MEN) supplemented with 10% heat inactivated calf serum (C$^i$) and 10% tryptose phosphate broth (Tp, Difco 0060). Cell cultures are used to produce live BTV from master seed virus obtained from Dr. T.L. Barber, USDA, Denver. Colorado. Cells are grown in culture vessels to 80% to 100% confluency (approximately $1 \times 10^5$ to $2 \times 10^5$ cells/cm$^2$ of growth surface area) using standard mammalian cell culture techniques. Generally, Corning plastic roller bottles (Corning No. 25140-850) with a growth surface area of 850 cm$^2$, containing 100 ml of MEN supplemented with 10% $C^i$ and 10% Tp and $1 \times 10^8$ to $2 \times 10^8$ CCL 10 cells per bottle are used for virus production. The cell cultures are initiated by seeding approximately $1 \times 10^6$ to $5 \times 10^7$ cells into 100 ml of growth medium in a roller bottle containing about 5% $CO_2$ in air and incubating the roller bottle on a roller bottle rotator at 1 to 5 rpm at 35° C. to 38° C. The cultures are grown to 80% to 100% confluency over a 7 to 14 day period with a 100% medium change every 2 to 4 days.

When the monolayers are 80% to 100% confluent the culture medium is removed and the monolayer is infected with approximately $1 \times 10^6$ to $2 \times 10^6$ plaqueforming units (pfu) of BTV in 20 ml of MEN with 2% heat-inactivated fetal bovine serum ($F^i$). The multiplicity of infection (MOI) is approximately 0.01. The virus inoculum is adsorbed to the cells by incubation at 35° C. to 38° C. for 1 hr. at 1 to 5 rpm. One hundred milliliters of MEN containing 10% $C^i$ and 10% Tp is added per roller bottle. The post-infection incubation is at 35° C. to 38° C. in 5% $CO_2$ in air with rotation. Two to four days post-infection, BTV cytopathic effect (CPE) is evident. The CPE is characterized by cell rounding, cell detachment, and cell degeneration. When at least 50% of the cell monolayer exhibits CPE the contents of the roller bottle are swirled or scraped with a rubber policeman to remove loosely attached materials from the roller bottle walls. The roller bottles and contents are incubated at 4° C. overnight. The harvest material is decanted into sterile centrifuge bottles. The virus, cells, and cell debris are pelleted by centrifugation at $2,000 \times g$ for 60 min., at 4° C.

The pellet is resuspended aseptically in 8 ml of 2 mM Tris-HCl, pH 8.8, for each original roller bottle. The suspension is mixed vigorously on a vortex mixer, and/or sonicated at 4° C. for 1 min., and centrifuged at $1,400 \times g$ for 30 min. at 4° C. The virus-containing supernatant is collected and the pellet is extracted twice more with 8 ml/roller bottle aliquots of 2 mM Tris-HCl, pH 8.8. The virus-containing supernatants are pooled and clarified by centrifugation at $4,000 \times g$ for 30 min. at 4° C. The clarified supernatant is stored at 4° C.

Virus Assay

Confluent monolayers of LMTK$^-$ or Vero (ATCC CCL 81) cells are prepared in 6 cm diameter mammalian cell culture plastic petri dishes (Corning #25010) or other convenient cell culture vessel. The growth medium used for LMTK$^-$ cell is alpha-modified Eagle's Minimum Essential Medium, Earle's Salts ($\alpha$ME)+10% $F^i$ and the growth medium used for Vero cells is MEN+5% $F^i$. Ten-fold serial dilutions of virus samples are made by adding 0.5 ml of the virus sample to 4.5 ml of phosphate buffered saline (PBS), pH 7.2 to 7.4+2% $F^i$ in a screw cap tube. The growth medium is removed from a 6 cm culture dish cell monolayer, 0.1 ml virus sample (undiluted or diluted) is added, and the virus is absorbed to the monolayer for 1 to 2 hrs. at 35° C. to 38° C. Two or more dishes are used for each sample. Five ml of overlay medium is added per 6 cm culture dish. The overlay medium is prepared by mixing equal parts of solution A (100 ml 2×MEM with L-glutamine, GIBCO #320-1935, +10 ml $F^i$) and 1.8% to 2% Noble Agar (Difco 0142) in deionized $H_2O$ at 44° C. to 45° C. The cultures are incubated at 35° C. to 38° C. in 5% $CO_2$ in air for 5 days. A second overlay containing Neutral Red at a final concentration of 0.005% is added on day 5. Plaques are counted on day 6 or day 7 post-infection. The virus titer in pfu/ml is calculated by multiplying the average number of plaques per dish by the reciprocal of the dilution. The pfu/ml is the value used to determine the amount of virus needed to infect cells at a MOI of approximately 0.01. The pfu/ml in a virus preparation prior to inactivation is used to determine the vaccine dose.

Inactivation Protocol

Twenty-five ml of BTV serotype 11 ($1.5 \times 10^8$ pfu/ml) is mixed with 0.25 ml of 4'-aminomethyl 4,5', 8-trimethylpsoralen (AMT; 1 mg/ml in DMSO). The mixture is placed in a 150 cm$^2$ tissue culture flask (T-150; Corning #25120). The viral suspension in the flask is placed in an argon atmosphere for 10 min. and then a stream of argon gas is blown over the viral suspension for an additional 2 min. The flask is tightly capped and the suspension is irradiated for 3.25 hours. at 4° C. using GE BLB fluorescent bulbs at an intensity of 1.5 mW/cm$^2$. An additional 0.25 ml of AMT is then added to the viral suspension, the suspension is transferred by pipet to a new T-150 flask, and the solution is again flushed with argon. The flask is irradiated for an additional 14.75 hrs. at 4° C. under the same long wavelength UV light source. After this irradiation an additional 0.25 ml of AMT solution is added to the suspension and it is again transferred to a new T-150 flask. The solution is flushed with argon as before and irradiated for an additional 5.5 hrs. at 4° C. The inactivated BTV is stored at 4° C.

Assessment of Inactivation by Blind Passage

CCL 10 cells are grown to confluency in 850 cm$^2$ roller bottles using standard cell culture procedures as described above. The culture medium is removed from the roller bottle and 2.0 ml of the inactivated virus preparation, mixed with 18 ml of medium containing 2% $F^i$, is adsorbed to the roller bottle cell monolayer for 60 min at 35° C. to 38° C. with rotation at 1 to 5 rpm. After adsorption the unabsorbed inoculum is removed and 100 ml of growth medium (MEN with 10% $C^i$ and 10% Tp) is added and the roller bottle culture incubated at 35° C. to 38° C. for 7 days with daily observation for viral CPE (see plaque assay above for description of CPE). The roller bottle culture should receive a 100% medium change every 2 to 3 days. If no CPE is observed during the first roller bottle passage, the cell monolayer is chilled at 4° C. for 12 to 24 hrs. The cells are scraped into the medium which is then decanted into a centrifuge bottle. The cells are pelleted by centrifugation at 4° C. at $2,000 \times g$ for 30 min. and resuspended in 2.0 ml of 2 mM Tris-HCl (pH 8.8) by vigorous mixing using a vortex mixer. The resuspended material is centrifuged at $2,000 \times g$ for 20 min. at 4° C. The supernatant is added to 18 ml of growth medium containing 2% $F^i$ and used to infect a new confluent roller bottle culture of CCL 10 cells as described immediately above. The second roller bottle blind passage is observed for 7 days and fed every 2 to 3 days. If no CPE is observed during the second roller bottle blind passage, a third roller bottle blind passage is performed. If no CPE has been observed by the end of the third roller bottle blind passage the virus preparation is considered inactivated.

EXAMPLE I

Four New Zealand white rabbits were randomly assigned to 2 groups, designated A and B. Both groups were given 4 immunizations at two week intervals. The first immunization consisted of 1 ml of vaccine ($10^8$ pfu BTV serotype 11) and 1 ml of Freund's Complete Adjuvant. The second through fourth immunizations utilized 1 ml of vaccine ($10^8$ pfu BTV serotype 11) and 1 ml of Freund's Incomplete Adjuvant. All immunizations were given intramuscularly (IM). The vaccine given to Group A (Vacciane #1) was inactivated with AMT-UVA in the presence of 0.01 M ascorbic acid. Vaccine #1 was dialyzed for 12 hours against 2 mM Tris, ph 8.6. The vaccine given to Group B (Vaccine #2) was inactivated with AMT-UVA without ascorbic acid and sonicated three times (2 minutes each time) using a cup horn probe (Heat Systems Model 431A) at a power setting of 3 (Heat Systems Model W220). Both Vaccine #1 and Vaccine #2 were deemed inactivated since no live virus was detected during blind passage. Inactivated vaccine was also tested for safety by chicken embryo inoculation. Egg deaths attributable to live virus were not encountered. Both rabbit groups were bled via auricular venipuncture one week following the second, third, and fourth immunizations. Serum from each rabbit was pooled with that of its groupmate, and the pooled sera were tested for anti-BTV antibodies by two standard serologic assays, serum neutralization (Jochim and Jones, *Am J. Vet. Res.* (1976) 37:1345–1347) and agar gel precipitation (Jochim *et al., Am. Assoc. Vet. Lab. Diag.,* *22nd Proceed.*: 463–471, 1979). Pre-immunization rabbit serum was used as the negative control; BTV immune sheep serum was used as the positive control for both immunologic procedures.

Pooled sera from Groups A and B reduced the number of viral plaques (serum neutralization) greater than eighty percent when the sera were diluted 1:40, which was the highest dilution examined. Negative and positive control sera behaved as expected.

TABLE 1

Serum Neutralization Data From Rabbits Vaccinated with AMT-UVA-inactivated Bluetongue Virus Vaccines.

| Group | Titer*: 1 | 5 | 40 |
|---|---|---|---|
| A | + | + | + |
| B | + | + | + |
| Normal Rabbit Serum | − | − | − |
| BTV-Immune Sheep Serum | + | + | ± |

*Reciprocal of serum dilution neutralizing 80 percent of BTV plaque activity on BHK cells. The data are from the post-second immunization serum samples.

Pooled post-immunization sera from Groups A and B precipitated BTV antigen in immunodiffusion plates when tested at dilutions up to 1:16. Normal rabbit serum did not precipitate the standard BTV antigen. BTV-immune sheep serum did precipitate the BTV antigen, but not at dilutions greater than 1:2.

Of the two immunologic procedures utilized, serum neutralization is predictive for immunity to live BTV challenge in the target species.

EXAMPLE II

Each of two adult sheep, known to be susceptible to BTV, were inoculated subcutaneously (SQ) with 2 ml of AMT-UVA inactivated BTV plus adjuvant (1:1; vaccine to aluminum hydroxide adjuvant). The vaccine contained approximately $10^8$ pfu/ml of BTV prior to inactivation. A third sheep was inoculated SQ with 6 ml of the identical vaccine without adjuvant. Seven weeks later the three sheep were given identical inoculations SQ that consisted of 5 ml of vaccine and aluminum hydroxide adjuvant (2:1 vaccine to adjuvant; $10^8$ pfu BTV/ml of vaccine).

The three sheep were monitored for clinical evidence of BTV, including daily body temperature recording and bi-daily virus isolation attempts. No evidence of BTV was observed, indicating that the vaccine was inactivated.

Serum was collected weekly for serum neutralization and agar gel precipitation testing. Normal sheep sera and BTV-immune sheep sera were used for negative and positive control samples in the serologic tests.

The first vaccine inoculations induced precipitating anti-BTV antibody in all three sheep. Their pre-exposure sera were uniformly negative for anti-BTV precipitating antibody. Modest neutralizing anti-BTV antibody titers (1:5) were elicited in two of three sheep following one immunization. The second immunization elicited a distinct immunologic anamnestic response, inducing neutralizing titers of 1:40, 1:80, or 1.1600 in the three sheep.

TABLE 2

Serum Neutralization Data From Sheep Immunized with an AMT-UVA Inactivated BTV Vaccine.

| | TITERS* Sheep No.: | | |
|---|---|---|---|
| | 1 | 2 | 3 |
| Pre-First Immunization | | | |
| Day 0 | <5 | <5 | <5 |
| Post-First Immunization | | | |
| Day 21 | 5 | 5 | <5 |
| Post-Second Immunization | | | |
| Day 7 | 80 | 160 | 40 |
| Day 14 | 80 | 40 | 40 |
| Day 21 | 80 | 80 | 40 |
| Day 42 | 80 | 80 | 80 |
| Post-Challenge | | | |
| Day 7 | 160 | 160 | 80 |
| Day 14 | 320 | 160 | 80 |

*Reciprocal of highest 2-fold dilution reducing BTV plaque activity on BHK cells by 80 percent.

The sheep were challenged by SQ syringe inoculation of $10^5$ egg lethal doses of BTV serotype 11. The three sheep remained clinically normal during the BTV challenge period, indicating that the vaccine was efficaceous.

It is evident from the above results that the BTV which is psoralen-inactivated retains its immunogenicity, particularly as to those sites which elicit an immune response which is effective in protecting a host against subsequent BTV-infection. Thus, the psoralen inactivation can be carried out under conditions which do not modify the immunogenic sites of the virus, so as to elicit an immunogenic response which will be effective against the live BTV. Furthermore, the BTV RNA virus is efficiently inactivated under mild conditions to the point of complete inactivation, whence it may be safely administered to a host.

Although the foregoing invention has been described in some detail by way of illustration and example for purposes of clarity of understanding, it will be obvious that certain changes and modifications may be practiced within the scope of the appended claims.

What is claimed is:

1. A vaccine useful for inoculation of a mammalian host susceptible to infection by Bluetongue virus (BTV), which comprises at least one furocoumarin-inactivated BTV serotype in from about $10^6$ to $10^9$ pfu/ml, wherein said inactivation is as a result of irradiation of BTV in the presence of an inactivating furocoumarin with long wavelength ultraviolet light at a temperature below about 40° C. for a time sufficient to inactivate said BTV to a non-infectious degree, and an immunologic adjuvant.

2. A vaccine according to claim 1, wherein said furocoumarin is 4'-aminomethyl-4,5',8-trimethylpsoralen.

3. A vaccine according to claim 2, wherein said BTV is of serotype 11.

4. A vaccine according to claim 1, wherein said BTV is inactivated in the presence of a singlet oxygen scavenger.

5. A vaccine according to claim 1, wherein said inactivation is performed in the substantial absence of oxygen.

6. A vaccine according to claim 1, wherein said BTV is grown in substantially confluent monolayers of cells immediately prior to inactivation.

7. A vaccine useful for inoculation of a mammalian host susceptible to infection by Bluetongue virus (BTV), which comprises BTV serotype 11 inactivated with 4'-aminomethyl-4,5',8-trimethylpsoralen by irradiation with long wavelength ultraviolet light at a temperature in the range of about $-10°$ to 25° C. for a time sufficient to inactivate said BTV to become non-infectious, said BTV being present in an amount of about $10^6$ to $10^9$ pfu/ml, and an immunologic adjuvant.

8. A vaccine useful for inoculation of a mammalian host susceptible to infection by Bluetongue virus (BTV), which comprises at least one furocoumarin-inactivated BTV serotype in from about $10^6$ to $10^9$ pfu/ml, wherein said inactivation is as a result of irradiation of BTV in the presence of an inactivating furocoumarin with long wavelength ultraviolet light at a temperature below about 40° C. for a time sufficient to inactivate said BTV to a non-infectious degree.

9. A vaccine useful for inoculation of a mammalian host susceptible to infection by Bluetongue virus (BTV), which comprises BTV serotype 11 inactivated with 4'-aminomethyl-4,5',8-trimethylpsoralen by temperature in the range of about $-10°$ to 25° C. for a time sufficient to inactivate said BTV to become non-infectious, said BTV being present in an amount of $10^6$ to $10^9$ pfu/ml.

10. A method for producing a vaccine for inoculation of a mammalian host susceptible to infection by bluetongue virus (BTV), which method comprises inactivating at least one BTV serotype by exposure to long wavelength ultraviolet light in the presence of a furocoumarin at a temperature below about 40° C. for a time sufficient to inactivate said BTV to a non-infectious degree, and combining said inactivated BTV with an appropriate adjuvant.

11. A method for producing a vaccine for inoculation of a mammalian host susceptible to infection by bluetongue virus (BTV), which method comprises exposure of at least one BTV serotype to long wavelength ultraviolet light in the presence of 4'-aminomethyl-4,5', 8-trimethylpsoralen at a temperature in the range from about $-10°$ C. to 25° C. for a time sufficient to inactivate the BTV to a non-infectious degree, and combining said inactivated BTV with a suitable adjuvant.

* * * * *